(12) United States Patent
Ishizuka et al.

(10) Patent No.: US 6,881,544 B2
(45) Date of Patent: Apr. 19, 2005

(54) METHOD OF AMPLIFYING OR DETECTING HIV-1 RNA

(75) Inventors: Tetsuya Ishizuka, Sagamihara (JP); Kiyoshi Yasukawa, Kawasaki (JP); Takahiko Ishiguro, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 85 days.

(21) Appl. No.: 10/126,611

(22) Filed: Apr. 22, 2002

(65) Prior Publication Data

US 2003/0008278 A1 Jan. 9, 2003

(30) Foreign Application Priority Data

Apr. 26, 2001 (JP) ........................................ 2001-129210

(51) Int. Cl.⁷ ........................... C12Q 1/68; C12P 19/34; C07H 21/04; C07H 21/02
(52) U.S. Cl. ........................ 435/6; 435/91.2; 536/22.1; 536/23.3
(58) Field of Search .................... 435/6, 91.2; 536/22.1, 536/23.3

(56) References Cited

U.S. PATENT DOCUMENTS

| | | |
|---|---|---|
| 5,374,524 A | 12/1994 | Miller |
| 5,707,864 A | 1/1998 | Essex et al. |

FOREIGN PATENT DOCUMENTS

| | | |
|---|---|---|
| EP | 0 806 484 | 11/1997 |
| EP | 0 969 101 | 1/2000 |
| WO | WO 93/08836 | 5/1993 |
| WO | WO 95/11701 | 5/1995 |

OTHER PUBLICATIONS

T. Kievits, et al., Journal of Virological Methods, vol. 35, No. 3, XP–000576430, pp. 273–286, NASBA™ Isothermal Enzymatic in Vitro Nucleic Acid Amplification Optimized for the Diagnosis of HIV–1 Infection.

S. Bruisten, et al., Aids Research and Human Retroviruses, vol. 9, No. 3, XP–002932546, pp. 259–266, "Detection of HIV–1 Distrubution in Different Blood Fractions by Two Nucleic Acid Amplification Assays", 1993.

J. W. Romano, et al., Clinics in Laboratory Medicine, vol. 16, No. 1, XP–000600141, pp. 89–103, "NASBA a Novel Isothermal Detection Technology For Qualitative and Quantitative HIV–1 RNA Measurements", Mar. 1, 1996.

*Primary Examiner*—Ethan Whisenant
*Assistant Examiner*—Joyce Tung
(74) *Attorney, Agent, or Firm*—Oblon, Spivak, McClelland, Maier & Neustadt, P.C.

(57) ABSTRACT

A simple, speedy and sensitive method of detecting HIV-RNA using an oligonucleotide which can bind to an intramolecularly free region of the genomic RNA of HIV-1 at relatively low and constant temperatures (at 35° C. to 50° C., preferably at 41° C.) as an oligonucleotide primer for use in amplification of a nucleic acid.

13 Claims, 4 Drawing Sheets

SEQUENCE LISTING

```
<160> NUMBER OF SEQ ID NOS: 35

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
actgtattat ataatgatct                                        20

<210> SEQ ID NO 2
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 2
attatataat gatctaagtt                                        20

<210> SEQ ID NO 3
<211> LENGTH: 20
<212> TYPE: DNA
<213> ORGANISM: Artificial Sequence
<220> FEATURE:
<223> OTHER INFORMATION: SYNTHETIC DNA
```

-continued

```
<400> SEQUENCE: 3
ataatgatct aagttcttct                                          20

<210> SEQ ID NO 4
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 4
gagggttgct actgtattat                                          20

<210> SEQ ID NO 5
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 5
caatagaggg ttgctactgt                                          20

<210> SEQ ID NO 6
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 6
gcacacaata gagggttgct                                          20

<210> SEQ ID NO 7
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 7
ttgctactgt attatataat                                          20

<210> SEQ ID NO 8
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 8
ggaaagaaaa aatataaatt aaaac                                    25

<210> SEQ ID NO 9
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 9
gaaaaaatat aaattaaaac atata                                    25

<210> SEQ ID NO 10
<211> LENGTH: 25
```

```
<212> TYPE: DNA
<213> ORGANISM: Artificial Sequence
<220> FEATURE:
<223> OTHER INFORMATION: SYNTHETIC DNA

<400> SEQUENCE: 10
aaaaatataa attaaaacat atagt                                    25

<210> SEQ ID NO 11
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 11
aaaatataaa ttaaaacata tagta                                    25

<210> SEQ ID NO 12
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 12
aaatataaat taaacatat agtat                                     25

<210> SEQ ID NO 13
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 13
aatataaatt aaaacatata gtatg                                    25

<210> SEQ ID NO 14
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 14
atataaatta aaacatatag tatgg                                    25

<210> SEQ ID NO 15
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 15
tataaattaa aacatatagt atggg                                    25

<210> SEQ ID NO 16
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 16
```
ataaattaaa acatatagta tgggc					25

<210> SEQ ID NO 17
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 17
aaattaaaac atatagtatg gcaa					25

<210> SEQ ID NO 18
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 18
aaaacatata gtatgggcaa gcagg					25

<210> SEQ ID NO 19
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 19
atatagtatg ggcaagcagg gagct					25

<210> SEQ ID NO 20
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 20
gtatgggcaa gcagggagct agaac					25

<210> SEQ ID NO 21
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 21 tttcccctg gccttaaccg					20

<210> SEQ ID NO 22
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 22
ttttctttcc ccctggcctt					20

<210> SEQ ID NO 23
<211> LENGTH: 20
<212> TYPE: DNA
<213> ORGANISM: Artificial Sequence

```
<220> FEATURE:
<223> OTHER INFORMATION: SYNTHETIC DNA

<400> SEQUENCE: 23 tttttttcttt cccccctggcc                                              20

<210> SEQ ID NO 24
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 24
attttttctt tccccctggc                                                20

<210> SEQ ID NO 25
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 25
tattttttct ttcccsctgg                                                20

<210> SEQ ID NO 26
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 26
atattttttc tttcccccctg                                               20

<210> SEQ ID NO 27
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 27 tatattttttt ctttcccct                                                20

<210> SEQ ID NO 28
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 28 ttatatttttt tctttccccc                                               20

<210> SEQ ID NO 29
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 29 tttatattttt ttctttcccc                                               20
```

```
<210> SEQ ID NO 30
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 30
aatttatatt ttttctttcc                                              20

<210> SEQ ID NO 31
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 31
gttttaattt atattttttc                                              20

<210> SEQ ID NO 32
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 32
tatatgtttt aatttatatt                                              20

<210> SEQ ID NO 33
<211> LENGTH: 20
<212> TYPE: DNA
<213> ORGANISM: Artificial Sequence
<220> FEATURE:
<223> OTHER INFORMATION: SYNTHETIC DNA

<400> SEQUENCE: 33
catactatat gttttaattt                                              20

<210> SEQ ID NO 34
<211> LENGTH: 19
<212> TYPE: DNA
<213> ORGANISM: Artificial Sequence
<220> FEATURE:
<223> OTHER INFORMATION: SYNTHETIC DNA

<400> SEQUENCE: 34
tctgaaggga tggttgtag                                               19

<210> SEQ ID NO 35
<211> LENGTH: 28
<212> TYPE: DNA
<213> ORGANISM: Artificial Sequence
<220> FEATURE:
<223> OTHER INFORMATION: SYNTHETIC DNA

<400> SEQUENCE: 35
aattctaata cgactcacta tagggaga                                     28
```

METHOD OF AMPLIFYING OR DETECTING HIV-1 RNA

The present invention relates to oligonucleotides used for amplification or detection of HIV-1 RNA in clinical tests and diagnoses.

Human immunodeficiency virus (HIV) is the pathogen of acquired immunodeficiency syndrome (AIDS). Two subtypes of HIV are known: HIV-1, which is spread worldwide, and HIV-2, which is epidemic mainly on the African West coast. The similarity between HIV-2 and simian immunodeficiency virus (SIV) in base sequence implies that HIV-2 may be zoonotic. However, clinical conditions of HIV-2 infection are less serious than those of HIV-1 infection.

HIV-1 infection induces production of antibodies against structural proteins and regulatory proteins of HIV-1. HIV-1 attacks the T cells classified as CD4+ lymphocytes as the main target immunocytes and hence abnormalizes the immune system in various ways. In the advanced stages of HIV-1 infection, B cells are stimulated to set off hypergammaglobulinemia, and autoantibodies and immunocomplexes appear with marked reduction of lymphocytes and blood platelets. Complications such as tuberculosis, Pneumocystis carinii pneumonia and other opportunistic infections at high levels of immunodeficiency induced by HIV-1 infection are diagnostic of onset of AIDS.

For diagnosis of HIV-1 infection, EIA (enzyme immunoassay) based on colorimetric detection of the reaction of an antibody against an viral antigen is available, coupled with Western blot confirmation of suspected positive serum samples by the presence of antibodies in the serum samples which react to a specific virus antigen in a blot of electrophoretically separated various virus particle antigens. However, assay methods which detect antibodies like this are not available for diagnoses of early stage infection before production of antibodies.

As discussed above, conventional assay methods can not afford diagnoses in the early stage of infection, require complicated operations and long time and can hardly detect a trace of HIV-1 in a sample in a short time. Therefore, development of a speedy and sensitive detection method is demanded. Especially, quantification of HIV-1 RNA is crucial to get information on pathological progress and the effectiveness of anti-HIV drugs. Further, development of automatic analyzers is demanded to facilitate clinical tests.

For high sensitive detection, it is preferred to amplify a specific sequence in a gene to be detected or identified or an RNA derived from such a gene before the detection. As a method of amplifying a specific sequence in RNAs like the HIV-1 genomic RNA, the reverse transcription-polymerase chain reaction (RT-PCR) is known. In this method, the reverse transcription step for synthesis of the cDNA of the target RNA is followed by repeated cycles of heat denaturation, primer-annealing and elongation reaction in the presence of a couple of primers, one of which is complementary to either end of the specific sequence and the other is homologous to the other end of the specific sequence (the antisense primer may be the same as the primer used in the reverse transcription step), and a thermostable DNA polymerase to give DNA as the amplification product of the specific sequence.

However, the necessity to conduct the operations in two steps (the reverse transcription step and the PCR step) and repeat the cumbersome operations such as rapid heating and cooling hinders automation of the RT-PCR.

NASBA or 3SR is known as a technique for amplifying a specific RNA sequence by the cooperative action of a reverse transcriptase and an RNA polymerase. This technique activates the chain reaction comprising synthesis of a double-stranded DNA having a promoter sequence from the target RNA by using a primer having a promoter sequence, a reverse transcriptase and ribonuclease H, and formation, by an RNA polymerase, of an RNA having the specific base sequence, which is then used as the template for synthesis of the above-mentioned double-stranded DNA having the promoter sequence, along the double-stranded DNA as the template. NASBA or 3SR allows relatively isothermal amplification of nucleic acid and is considered suitable for automation.

However, since the reactions involved in this amplification technique are carried out at relatively low temperatures (for example, at 41° C.), it is possible that the formation of an intramolecular structure of the target RNA lowers the reaction efficiency by hindering binding of the primers. Therefore, an operation of destroying the intramolecular structure of the target RNA such as heat denaturation of the target RNA is necessary before the amplification reaction to increase the binding efficiency of the primers.

The object of the present invention is to provide a simple, speedy and sensitive method of amplifying or detecting HIV-RNA through provision of an oligonucleotide which can bind to an intramolecularly free region of the genomic RNA of HIV-1 at relatively low and constant temperatures (at 35° C. to 50° C., preferably at 41° C.) as an oligonucleotide primer for use in amplification of a nucleic acid.

The present invention has been accomplished to attain the above-mentioned objects. The invention defined in a first embodiment of the present application provides a step of amplifying an RNA derived from HIV-1, which comprises synthesizing a cDNA by the action of an RNA-dependent DNA polymerase by using a specific sequence in an RNA derived from HIV-1 anticipated in a sample as a template, a first primer containing a sequence complementary to the specific sequence and a second primer containing a sequence homologous to the specific sequence (either of which additionally has a promoter sequence for the RNA polymerase at the 5' end), denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA as a template by the action of a DNA-dependent DNA polymerase, and then transcribing the double-stranded DNA into an RNA transcript, which acts as a template in the subsequent cDNA synthesis by the RNA-dependent DNA polymerase, in the presence of the RNA polymerase, wherein the first primer is an oligonucleotide of any one of SEQ ID NOS: 1 to 7, and the second primer is an oligonucleotide of any one of SEQ ID NOS: 8 to 20.

The invention defined in a second embodiment of the present application provides the step according to the first embodiment, which further comprises adding a third oligonucleotide which is complementary to a region of the RNA derived from HIV-1 which flanks the 5' end of the specific sequence with an overlap (of from 1 to 10 bases) with the specific sequence to form a template used in the initial stage of the amplification by cutting the RNA derived from HIV-1 at the 5' end of the specific sequence (by the action of the rebonuclease H), wherein the first primer is an oligonucleotide of any one of SEQ ID NOS: 1 to 7, and (1) the second primer is an oligonucleotide of SEQ ID NO: 8, and the third oligonucleotide is an oligonucleotide of any one of SEQ ID NOS: 21 and 22, (2) the second primer is an oligonucleotide of SEQ ID NO: 9, and the third oligonucleotide is an oligonucleotide of any one of SEQ ID NOS: 22 to 26, (3) the second primer is an oligonucleotide of SEQ ID NO: 10, and the third oligonucleotide is an oligonucleotide of any one of SEQ ID NOS: 22 to 28, (4) the second primer is an oligonucleotide of SEQ ID NO: 11, and the third oligonucleotide is an oligonucleotide of any one of SEQ ID NOS: 22 to 29, (5) the second primer is an oligonucleotide of SEQ ID NO: 12, and the third oligonucleotide is an oligonucleotide of any one of SEQ ID NOS: 22 to 29, (6) the second primer is an oligonucleotide of SEQ ID NO: 13, and the third oligonucleotide is an oligonucleotide of any one of SEQ ID NOS: 23 to 30, (7) the second primer is an oligonucleotide of SEQ ID NO: 14, and the third oligonucleotide is an oligonucleotide of any one of SEQ ID NOS: 23 to 30, (8) the second primer is an oligonucleotide of SEQ ID NO: 15, and the third oligonucleotide is an oligonucleotide of any one of SEQ ID NOS: 24 to 30, (9) the second primer is an oligonucleotide of SEQ ID NO: 16, and the third oligonucleotide is an oligonucleotide of any one of SEQ ID NOS: 25 to 30,

(10) the second primer is an oligonucleotide of SEQ ID NO: 17, and the third oligonucleotide is an oligonucleotide of any one of SEQ ID NOS: 27 to 31,

(11) the second primer is an oligonucleotide of SEQ ID NO: 18, and the third oligonucleotide is an oligonucleotide of any one of SEQ ID NOS: 31 and 32,

(12) the second primer is an oligonucleotide of SEQ ID NO: 19, and the third oligonucleotide is an oligonucleotide of any one of SEQ ID NOS: 32 and 33, or

(13) the second primer is an oligonucleotide of SEQ ID NO: 20, and the third oligonucleotide is an oligonucleotide of SEQ ID NO: 33.

The invention defined in a third embodiment of the present application provides a step of detecting HIV-1, which comprises conducting the step as defined in the first or second embodiment in the presence of an oligonucleotide probe (having a sequence different from those of the first primer and the second primer) which can specifically bind to the RNA transcript resulting from the amplification and is labeled with a fluorescent intercalative dye, and measuring the change in the fluorescence from the reaction solution.

The invention defined in a fourth embodiment of the present application provides the step according to the third embodiment, wherein the oligonucleotide probe is designed to hybridize with at least part of the RNA transcript and alters its fluorescence upon hybridization.

The invention defined in a fifth embodiment of the present application provides the step according to the fourth embodiment, wherein the oligonucleotide probe has a sequence consisting of or complementary to at least 10 consecutive bases in SEQ ID NO: 34.

Figure 1:
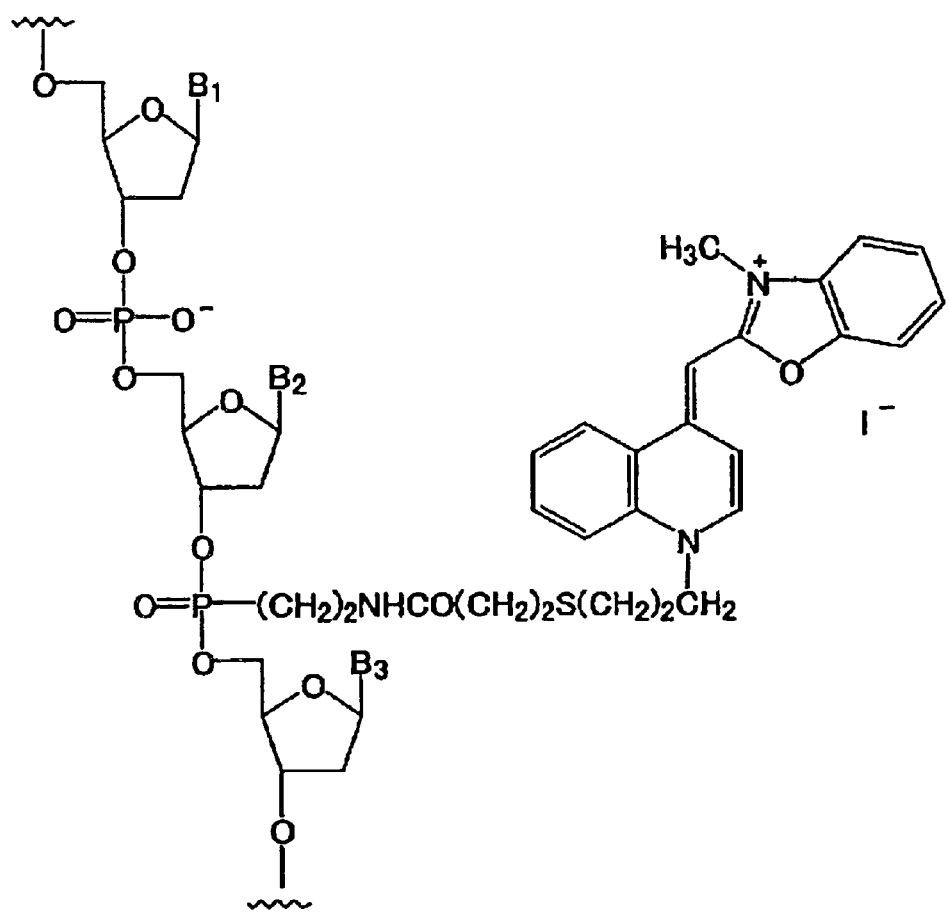
FIG. 1 is the chemical formula of the fluorescent intercalative dye moiety of the fluorescent intercalative dye-labeled oligonucleotide used in Example 2. $B_1$ to $B_3$ are nucleic acid bases.

Now, the present invention will be described in detail.

The present invention provides a nucleic acid amplification step for amplification of HIV-RNA in a sample, and a method of detecting the RNA transcript formed by the nucleic acid amplification step. The amplification step of the present invention covers any amplification methods such as PCR, NASBA or 3SR. However, isothermal nucleic acid amplification such as NASBA or 3SR by the cooperative action of a reverse transcriptase and an RNA polymerase (under such conditions that the reverse transcriptase and the RNA polymerase act cooperatively) is preferred for amplifying a specific RNA sequence in HIV-1.

For example, NASBA amplification of an RNA comprises synthesizing a cDNA by the action of an RNA-dependent DNA polymerase by using a specific sequence in HIV-1 RNA in a sample as the template, denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA as the template by the action of a DNA-dependent DNA polymerase, and then transcribing the double-stranded DNA into an RNA transcript, which acts as a template in the subsequent cDNA synthesis by the RNA-dependent DNA polymerase, in the presence of an RNA polymerase. The present invention is characterized by the use of an oligonucleotide primer of any one of SEQ ID NOS:1 to 7 as a first primer, which can bind to a specific site of the HIV-1 RNA and an oligonucleotide of any one of SEQ ID NOS:8 to 20 as a second primer, which is homologous to part of the HIV-1 RNA to be amplified (either of which additionally has a promoter sequence for the RNA polymerase at the 5' end).

One embodiment of the present invention is the above-mentioned amplification step wherein the first primer is an oligonucleotide of any one of SEQ ID NOS:1 to 7, and the second primer is an oligonucleotide of any one of SEQ ID NOS:8 to 20 (provided that either the first primer or the second primer additionally has a promoter sequence for the RNA polymerase at the 5' end). The RNA-dependent DNA polymerase, the DNA-dependent DNA polymerase and the ribonuclease H are not particularly limited, but AMV reverse transcriptase is preferable because it has the activities of all of them. As the RNA polymerase, T7 phage RNA polymerase or SP6 phage RNA polymerase is preferred, though there is no particular restriction.

In the above-mentioned amplification step, even if the specific sequence is not present at the 5' end, HIV-1 RNA can be amplified by adding an oligonucleotide complementary to a region of HIV-1 RNA which flanks the 5' end of the specific sequence with an overlap (of from 1 to 10 bases) with the specific sequence to cleave HIV-1 RNA at the 5' end (by the action of a ribonuclease H) before it is used as the template in the initial stage of the nucleic acid amplification. As the scissor oligonucleotide, an oligonucleotide of any of SEQ ID NOS:21 to 33 may be used. The scissor oligonucleotide is preferred to have a chemically modified hydroxyl group (for example, an aminated hydroxyl group) at the 3' end and not to elongate from the 3' end.

All When the third oligonucleotide complementary to a region which flanks the 5' end of the specific sequence with a (1 to 10-base) overlap with the specific sequence as mentioned above is added to cleave HIV-1 RNA at the 5' end (by the action of a ribonuclease H) before it is used as the template in the initial stage of the nucleic acid amplification, it is preferred that the first primer is an oligonucleotide of any one of SEQ ID NOS:1 to 7, and (1) the second primer is an oligonucleotide of SEQ ID NO:8, and the third oligonucleotide is an oligonucleotide of any one of SEQ ID NOS:21 and 22, (2) the second primer is an oligonucleotide of SEQ ID NO:9, and the third oligonucleotide is an oligonucleotide of any one of SEQ ID NOS:22 to 26, (3) the second primer is an oligonucleotide of SEQ ID NO:10, and the third oligonucleotide is an oligonucleotide of any one of SEQ ID NOS:22 to 28, (4) the second primer is an oligonucleotide of SEQ ID NO:11, and the third oligonucleotide is an oligonucleotide of any one of SEQ ID NOS:22 to 29, (5) the second primer is an oligonucleotide of SEQ ID NO:12, and the third oligonucleotide is an oligonucleotide of any one of SEQ ID NOS:22 to 29, (6) the second primer is an oligonucleotide of SEQ ID NO:13, and the third oligonucleotide is an oligonucleotide of any one of SEQ ID NOS:23 to 30, (7) the second primer is an oligonucleotide of SEQ ID NO:14, and the third oligonucleotide is an oligonucleotide of any one of SEQ ID NOS:23 to 30, (8) the second primer is an oligonucleotide of SEQ ID NO:15, and the third oligonucleotide is an oligonucleotide of any one of SEQ ID NOS:24 to 30, (9) the second primer is an oligonucleotide of SEQ ID NO:16, and the third oligonucleotide is an oligonucleotide of any one of SEQ ID NOS:25 to 30,

(10) the second primer is an oligonucleotide of SEQ ID NO:17, and the third oligonucleotide is an oligonucleotide of any one of SEQ ID NOS:27 to 31,

(11) the second primer is an oligonucleotide of SEQ ID NO:18, and the third oligonucleotide is an oligonucleotide of any one of SEQ ID NOS:31 and 32,

(12) the second primer is an oligonucleotide of SEQ ID NO:19, and the third oligonucleotide is an oligonucleotide of any one of SEQ ID NOS:32 and 33, or

(13) the second primer is an oligonucleotide of SEQ ID NO:20, and the third oligonucleotide is an oligonucleotide of SEQ ID NO:33.

In this case, the third oligonucleotide (the scissor oligonucleotide) is preferred to have a chemically modified hydroxyl group (for example, an aminated hydroxyl group) at the 3' end not to elongate from the 3' end, too.

Detection of the amplification product obtained in the nucleic acid amplification step is preferably carried out by measuring the change in the fluorescence of the reaction solution during the amplification step in the presence of an oligonucleotide probe labeled with a fluorescent intercalative dye, though it can be detected by conventional methods for detection of nucleic acid. The oligonucleotide probe may be, for example, an oligonucleotide having a fluorescent intercalative dye linked to a phosphorus atom via a linker. Such a preferable probe alters its fluorescence upon formation of a double strand with the target nucleic acid (a complementary nucleic acid) through intercalation of the intercalator moiety to the double strand (Ishiguro, T. et al., (1996) Nucleic Acids Res. 24 (24) 4992–4997).

The sequence of the probe is not particularly limited as long as it contains a sequence complementary to at least part of the RNA transcript. For example, when the combination of a first primer of any one of SEQ ID NOS:1 to 7 and a second primer of any one of SEQ ID NOS:8 to 20, is used in the RNA amplification step, a sequence consisting of or complementary to at least 10 consecutive bases in SEQ ID NO:34 is preferred. In this case, it is also preferred to chemically modify the hydroxyl group at the 3' end of the probe (for example, by adding glycolic acid) to prevent elongation reaction using the probe as a primer.

By carrying out the amplification step in the presence of the above-mentioned probe, amplification and detection of HIV-1 RNA can be carried out at constant temperature in one tube in one step and can be automated easily.

Now, the present invention will be described in further detail by referring to Examples. However, the present invention is by no means restricted to these specific Examples.

EXAMPLE 1

The target HIV-RNA derived from various numbers of initial copies was detected using the combinations of oligonucleotides in the present invention.

(1) A 1628-nt RNA base sequence in the HIV-1 RNA base sequence containing the structural gene of the core protein (gag) was used as a standard RNA. The standard RNA was obtained from HIV-1 RNA with ACCRUN™ 315 (product name), HIV-1 RNA Positive Control, Series 400 (BBI (Boston Biomedica, Inc.) by conventional extraction and synthesis of a double-stranded DNA containing the base sequence of the gag region by RT-PCR and in vitro transcription using the DNA as the template and purified.

(2) The standard RNA was quantified by UV absorptiometry at 260 nm and diluted with an RNA diluent (10 mM Tris-HCl (pH 8.0), 0.1 mM EDTA, 1 mM DTT, 0.5 U/μl RNase inhibitor (Takara Shuzo Co., Ltd.)) to $10^5$ copies/5 μl, $10^4$ copies/ 5 μl, $10^3$ copies/5 μl, $10^2$ copies/5 μl and 10 copies/5 μl. The diluent alone was used as a control sample (Nega).

(3) 20.8 μl portions of a reaction solution of the following composition were dispensed into 0.5 ml PCR tubes (Gene Amp Thin-Walled Reaction Tubes, Perkin Elmer), and 5 μl of the RNA sample at the above-mentioned concentrations was added.

The composition of the reaction solution (in terms of the concentrations in the final volume of 30 μl)

| | |
|---|---|
| 60 mM | Tris-HCl buffer (pH 8.6) |
| 13 mM | Magnesium chloride |
| 115 mM | Potassium chloride |
| 39 U | RNase Inhibitor |
| 1 mM | DTT |
| 0.25 mM | each of dATP, dCTP, dGTP and dTTP |
| 3.6 mM | ITP |

-continued

| | |
|---|---|
| 3.0 mM | each of ATP, CTP, GTP and UTP |
| 1.0 μM | First primer (SEQ ID NO: 1) |
| 1.0 μM | Second primer (SEQ ID NO: 15) (which had a base sequence (SEQ ID NO: 35) including the T7 promoter sequence at the 5' end (SEQ ID NO: 35 comprises the T7 promoter sequence from "A" at position 1 from the 5' end to "A" at position 22 and the subsequent enhancer sequence from "G" at position 23 to "A" at position 28) |
| 0.16 μM | Third oligonucleotide (SEQ ID NO: 27) |
| 25 nM | Oligonucleotide (SEQ ID NO: 34) labeled with a fluorescent intercalative dye (FIG. 1) (having the fluorescent intercalative dye between "T" at position 14 from the 5' end and "T" at position 15 and having a hydroxyl group modified with glycolic acid at the 3' end) |
| 13% DMSO | |
| Distilled water for volume adjustment | |

(4) The reaction solutions were incubated at 41° C. for 5 minutes, and 4.2 μl of an enzyme solution of the following composition which was pre-incubated at 41° C. for 2 minutes was added.

The composition of the enzyme solution (in terms of the concentrations in the final volume of 30 μl)

| | |
|---|---|
| 1.7% | Sorbitol |
| 3 μg | Bovine serum albumin |
| 142 U | T7 RNA polymerase (GIBCO) |
| 8 U | AMV reverse transcriptase (Takara Shuzo Co., Ltd.) |
| Distilled water for volume adjustment | |

(5) The fluorescence intensities of the reaction solutions in the PCR tubes were directly monitored at 41° C. in a thermostatic fluorescent spectrophotometer at an excitation wavelength of 470 nm and an emission wavelength of 510 nm. The time courses of the ratio of fluorescence intensities of the samples (fluorescence intensity at a certain time/ background fluorescence intensity) from addition of the enzyme solution at 0 minute were shown in FIG. 2. The initial amounts of the RNA were from 10 copies/30 μl to $10^5$ copies/30 μl.

Figure 2:
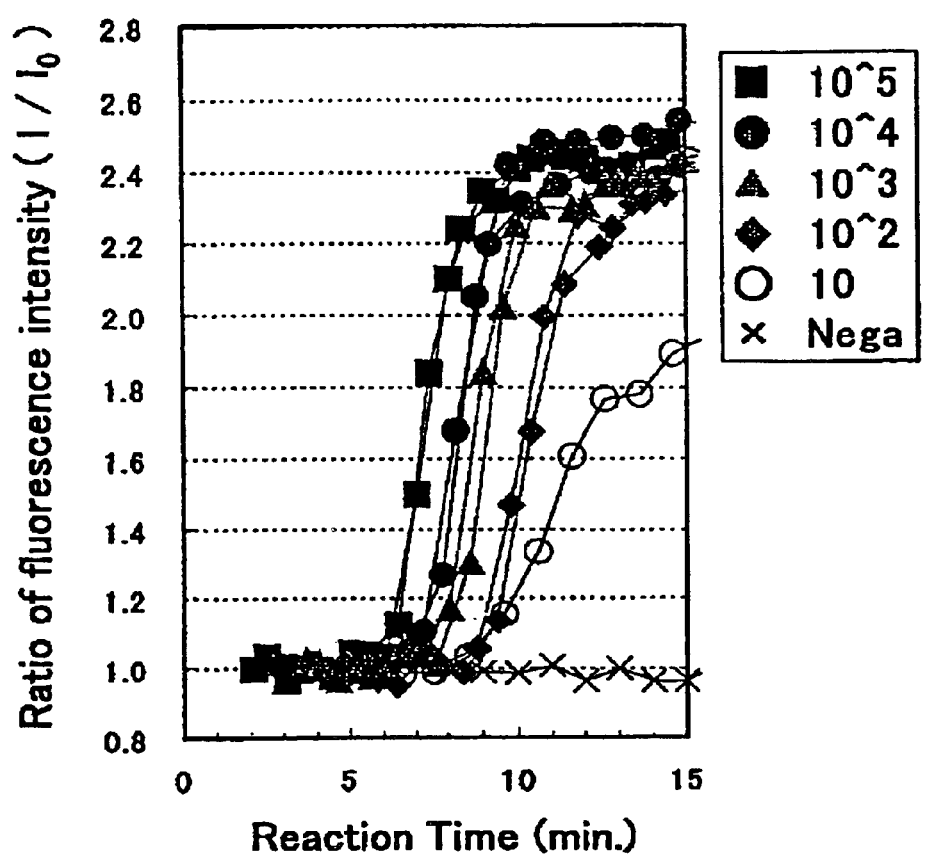
FIG. 2 is a graph correlating the reaction time and the fluorescence enhancement accompanying RNA synthesis at initial RNA amounts of $10^5$ copies/30 µl to 10 copies/30 µl in Example 1. Nega indicates a sample prepared by using a diluent instead of the RNA sample.
Figure 3:
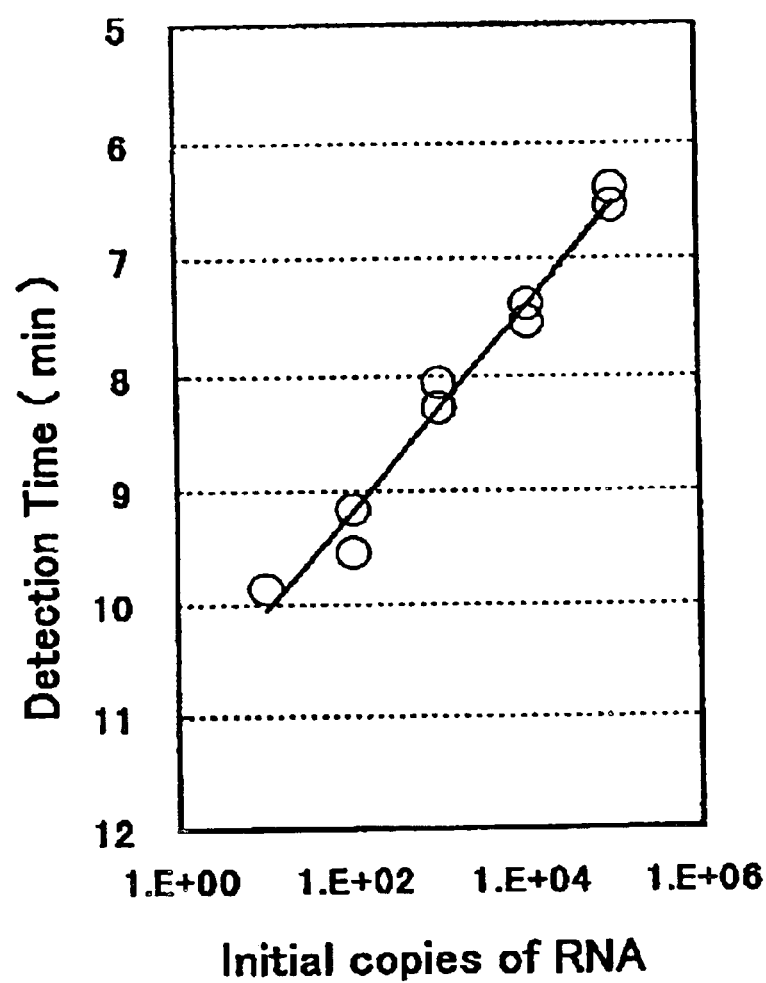
FIG. 3 is a calibration curve obtained by plotting the detection time, which is defined as the time at the ratio of fluorescent intensity of 1.2, as ordinate and the initial RNA concentration as abscissa.

As shown in FIG. 2, the fluorescence profile was dependent on the initial concentration of the standard RNA, and it was possible to detect 10 copies in about 10 minutes. When the detection time, which is defined as the time at the ratio of fluorescent intensity of 1.2, was plotted as ordinate, and the initial RNA concentration was plotted as abscissa, a linear relation was found between them (FIG. 3), and it was indicated that it is possible to quantify HIV-1 RNA in an unknown sample by using FIG. 3 as the calibration curve. Thus, it is proved that the present invention allows speedy and sensitive quantitative detection of HIV-1 RNA.

EXAMPLE 2

HIV-1 RNA in the nucleic acid extracted from HIV-positive serum was detected using the combinations of oligonucleotides in the present invention.

(1) As the HIV-positive serum, ACCRUN™ 315 (product name), HIV-1 RNA Positive Control, Series 400 (BBI (Boston Biomedica, Inc.) was used. HIV-1 RNA was obtained from 30 μl of the positive serum by conventional extraction and diluted with an RNA diluent (10 mM Tris-HCl (pH 8.0), 0.1 mM EDTA, 1 mM DTT, 0.5 U/μl RNase inhibitor (Takara Shuzo Co., Ltd.)) to an estimated RNA amount of $10^3$ copies/5 μl. The same standard RNA as in Example 1 was used at a concentration of $10^3$ copies/5 μl.

(2) A 20.8 μl portion of a reaction solution of the following composition was dispensed into a 0.5 ml PCR tube (Gene Amp Thin-Walled Reaction Tubes, Perkin Elmer), and 5 μl of the RNA sample at the above-mentioned concentration was added.

The composition of the reaction solution (in terms of the concentrations in the final volume of 30 μl)

| | |
|---|---|
| 60 mM | Tris-HCl buffer (pH 8.6) |
| 13 mM | Magnesium chloride |
| 115 mM | Potassium chloride |
| 39 U | RNase Inhibitor |
| 1 mM | DTT |
| 0.25 mM | each of dATP, dCTP, dGTP and dTTP |
| 3.6 mM | ITP |
| 3.0 mM | each of ATP, CTP, GTP and UTP |
| 1.0 μM | First primer (SEQ ID NO: 2) |
| 1.0 μM | Second primer (SEQ ID NO: 13) (which had a base sequence (SEQ ID NO: 35) including the T7 promoter sequence at the 5' end (SEQ ID NO: 35 comprises the T7 promoter sequence from "A" at position 1 from the 5' end to "A" at position 22 and the subsequent enhancer sequence from "G" at position 23 to "A" at position 28) |
| 0.16 μM | Third oligonucleotide (SEQ ID NO: 26) |

| | |
|---|---|
| 25 nM | Oligonucleotide (SEQ ID NO: 34) labeled with a fluorescent intercalative dye (FIG. 1) (having the fluorescent intercalative dye between "T" at position 14 from the 5' end and "T" at position 15 and having a hydroxyl group modified with glycolic acid at the 3' end) |
| 13% DMSO | |
| Distilled water for volume adjustment | |

(3) The reaction solution was incubated at 41° C. for 5 minutes, and 4.2 µl of an enzyme solution of the following composition which was pre-incubated at 41° C. for 2 minutes was added.

The composition of the enzyme solution (in terms of the concentrations in the final volume of 30 µl)

| | |
|---|---|
| 1.7% | Sorbitol |
| 3 µg | Bovine serum albumin |
| 142 U | T7 RNA polymerase (GIBCO) |
| 8 U | AMV reverse transcriptase (Takara Shuzo Co., Ltd.) |
| Distilled water for volume adjustment | |

(4) The fluorescence instensity of the reaction solution in the PCR tube was directly monitored at 41° C. in a thermostatic fluorescent spectrophotometer at an excitation wavelength of 470 nm and an emission wavelength of 510 nm. The time course of the ratio of fluorescence intensity of the sample (fluorescence intensity at a certain time/background fluorescence intensity) from addition of the enzyme solution at 0 minute was shown in FIG. 4.

Figure 4:
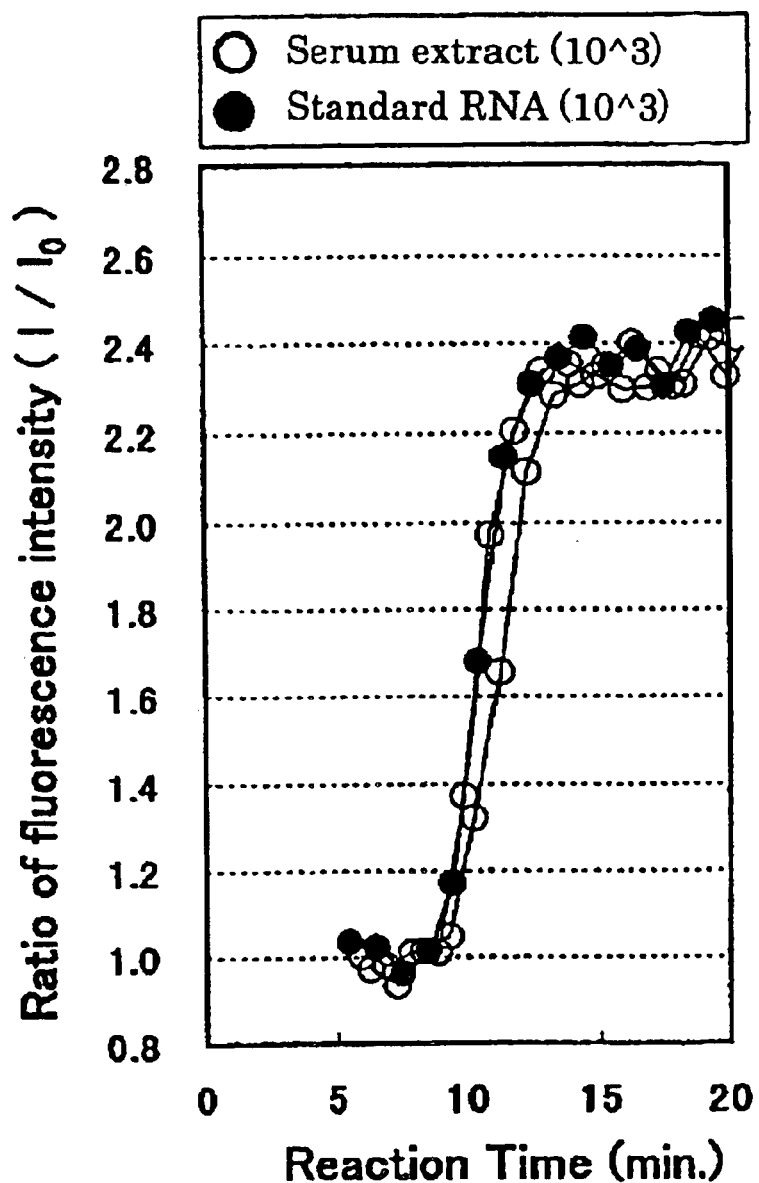
FIG. 4 is a graph correlating the reaction time and the fluorescence enhancement in the detection of HIV-RNA in the nucleic acid extracted from HIV-positive serum in Example 2.

FIG. 4 demonstrates that it was possible to detect the RNA (at an estimated concentration of $10^3$ copies/30 µl) extracted from the HIV-positive serum at the same detection time as the standard RNA (RNA concentration: $10^3$ copies/30 µl) as the control.

Thus, it is proved that the present invention allows speedy and sensitive detection of HIV-1 RNA extracted from HIV-positive serum.

As described above, the present invention provide a simple, speedy and sensitive method of detecting HIV-RNA through provision of an oligonucleotide which can bind to an intramolecularly free region of the genomic RNA of HIV-1 at relatively low and constant temperatures (at 35° C. to 50° C., preferably at 41° C.) as an oligonucleotide primer for use in amplification of a nucleic acid.

The entire disclosure of Japanese Patent Application No. 2001-129210 filed on Apr. 26, 2001 including specification, claims, drawings and summary are incorporated herein by reference in its entirety.

What is claimed is:

1. A method for amplifying HIV-1 RNA in a sample comprising: contacting a sample containing HIV-1 RNA with a set of primers under conditions suitable for transcription and amplification of HIV-1 nucleic acid, wherein said set of primers comprises SEQ ID NO: 2 and SEQ ID NO: 13.

2. The method of claim 1, wherein one primer in said set further comprises a promoter for RNA polymerase at the 5' end.

3. The method of claim 1 further comprising synthesizing a cDNA by the action of an RNA-dependent DNA polymerase by using a specific sequence in an RNA derived from HIV-1 anticipated in a sample as a template, and using a first primer containing a sequence complementary to the specific sequence and a second primer containing a sequence homologous to the specific sequence (either of which additionally has a promoter sequence for the RNA polymerase at the 5' end), denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA as a template by the action of a DNA-dependent DNA polymerase, and then transcribing the double-stranded DNA into an RNA transcript, which acts as a template in the subsequent cDNA synthesis by the RNA-dependent DNA polymerase, in the presence of the RNA polymerase.

4. The method of claim 1, further comprising using a third oligonucleotide which is complementary to a region of the RNA derived from HIV-1 which flanks the 5' end of the specific sequence with an overlap (of from 1 to 10 bases) with the specific sequence to form a template used in the initial stage of the amplification by cutting the RNA derived from HIV-1 at the 5' end of the specific sequence (by the action of the ribonuclease H).

5. The method of claim 1, wherein transcription and amplification comprise the use of T7 phage RNA polymerase and AMV reverse transcriptase.

6. A method for detecting HIV-1 RNA in a sample comprising:

contacting a sample suspected of containing HIV-1 RNA with a set of primers under conditions suitable for transcription and amplification of HIV-1 nucleic acid, and detecting the presence of amplified HIV-1 nucleic acids, wherein said set of primers comprises SEQ ID NO: 2 and SEQ ID NO: 13.

7. The method of claim 6, wherein one primer in said set further comprises a promoter for RNA polymerase at the 5' end.

8. The method of claim 6, further comprising:

synthesizing a cDNA by the action of an RNA-dependent DNA polymerase by using a specific sequence in an RNA derived from HIV-1 anticipated in a sample as a template, and using a first primer containing a sequence complementary to the specific sequence and a second primer containing a sequence homologous to the specific sequence (either of which additionally has a promoter sequence for the RNA polymerase at the 5' end), denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA as a template by the action of a DNA-dependent DNA polymerase, and then transcribing the double-stranded DNA into an RNA transcript, which acts as a template in the subsequent cDNA synthesis by the RNA-dependent DNA polymerase, in the presence of the RNA polymerase.

9. The method of claim 6, further comprising using a third oligonucleotide which is complementary to a region of the RNA derived from HIV-1 which flanks the 5' end of the specific sequence with an overlap (of from 1 to 10 bases) with the specific sequence to form a template used in the initial stage of the amplification by cutting the RNA derived from HIV-1 at the 5' end of the specific sequence (by the action of the ribonuclease H).

10. The method of claim 6, wherein transcription and amplification comprise the use of T7 phage RNA polymerase and AMV reverse transcriptase.

11. The method of claim 6, comprising detecting the presence of amplified HIV-1 nucleic acid by contacting said sample with an oligonucleotide probe and measuring the change in the fluorescence from the reaction solution, wherein said probe is labeled with a fluorescent intercalative dye, has a sequence different than the first or second primer, and can bind to an HIV-1 transcript resulting from said amplification.

12. The method of claim 11, wherein the oligonucleotide probe hybridizes with at least part of the RNA transcript and alters its fluorescence upon hybridization.

13. The method of claim 11, wherein the oligonucleotide probe consists of at least 10 consecutive bases of SEQ ID NO: 34 or consists of at least 10 consecutive bases of the full complement of SEQ ID NO: 34.

* * * * *